United States Patent [19]

Mamenta et al.

[11] Patent Number: 5,435,970
[45] Date of Patent: Jul. 25, 1995

[54] DEVICE FOR ANALYSIS FOR CONSTITUENTS IN BIOLOGICAL FLUIDS

[75] Inventors: Edward L. Mamenta, Carrboro; Michael F. Turnachik, Gibsonville, both of N.C.

[73] Assignee: Environmental Diagnostics, Inc., Burlington, N.C.

[21] Appl. No.: 917,921

[22] Filed: Jul. 21, 1992

Related U.S. Application Data

[63] Continuation of Ser. No. 451,768, Dec. 18, 1989, abandoned.

[51] Int. Cl.$^6$ .......................................... G01N 21/78
[52] U.S. Cl. ........................................ 422/56; 422/58; 422/100; 435/11; 435/14; 435/805
[58] Field of Search ................ 422/56, 58, 52, 66, 422/100; 435/11, 14, 805, 7.1, 7.72, 7.9; 436/71, 513, 536

[56] References Cited

U.S. PATENT DOCUMENTS

| | | |
|---|---|---|
| 3,552,925 | 1/1971 | Fetter . |
| 3,791,933 | 2/1974 | Moyer et al. ............ 435/14 X |
| 3,844,717 | 10/1974 | Sodickson et al. ............ 422/52 |
| 3,902,964 | 9/1975 | Greenspan ............ 435/14 |
| 3,917,453 | 11/1975 | Milligan et al. ............ 422/56 X |
| 3,964,871 | 6/1976 | Hochstrasser . |
| 3,983,005 | 9/1976 | Goodhue et al. . |
| 4,042,329 | 9/1977 | Hochstrasser . |
| 4,160,008 | 7/1979 | Fenochetti . |
| 4,189,304 | 2/1980 | Adams, Jr. et al. ............ 422/56 X |
| 4,256,693 | 3/1981 | Kondo et al. ............ 422/57 X |
| 4,435,504 | 3/1984 | Zuk et al. . |
| 4,477,575 | 10/1984 | Vogel et al. . |
| 4,594,327 | 7/1986 | Zuk . |
| 4,678,757 | 7/1987 | Rapkin et al. . |
| 4,696,797 | 9/1987 | Kelton ............ 422/58 X |
| 4,753,776 | 6/1988 | Hillman et al. ............ 210/505 X |
| 4,780,280 | 10/1988 | Berger et al. ............ 422/58 |
| 4,820,489 | 4/1989 | Rothe et al. ............ 422/58 |
| 4,826,759 | 5/1989 | Guire et al. ............ 422/58 |
| 4,883,764 | 11/1989 | Kloepfer ............ 422/58 |
| 4,891,313 | 1/1990 | Berger et al. ............ 435/7.94 |
| 4,900,663 | 2/1990 | Wie et al. ............ 422/58 X |
| 4,933,092 | 6/1990 | Aunet et al. ............ 436/177 X |
| 4,973,549 | 11/1990 | Khanna et al. ............ 435/11 |
| 4,987,085 | 1/1991 | Allen et al. ............ 422/57 |

FOREIGN PATENT DOCUMENTS 3441149 5/1986 Germany .
3508427 9/1986 Germany .

OTHER PUBLICATIONS

"The Quantab Strip In The Measurement Of Urinary Chloride and Sodium Concentrations" Sloan et al, *Clin. Chem.* 30 (10), 1705–1707 (1984).

*Primary Examiner*—James C. Housel
*Assistant Examiner*—Arlen Soderquist
*Attorney, Agent, or Firm*—John L. Sigalos

[57] ABSTRACT

The invention is a device for separating blood cells from biological fluids, preferably plasma from whole blood. The invention includes a nonabsorbent, porous unitary support, which is desirably made of glass fiber, and a blood cell binding composition, such as a lectin. This device provides a test kit for measuring a plasma analyte in whole blood. This kit separates plasma from the whole blood, exposes the plasma to reactants that detect an analyte, and provides a chromatic or other result in response to exposure to the analyte. A desirable embodiment of the device has a cover plate over the reaction pad to apply uniaxialy pressure to the reaction pad which controls migration of plasma. The invention includes a method for separating plasma from whole blood and a method for detecting an analyte.

13 Claims, 5 Drawing Sheets

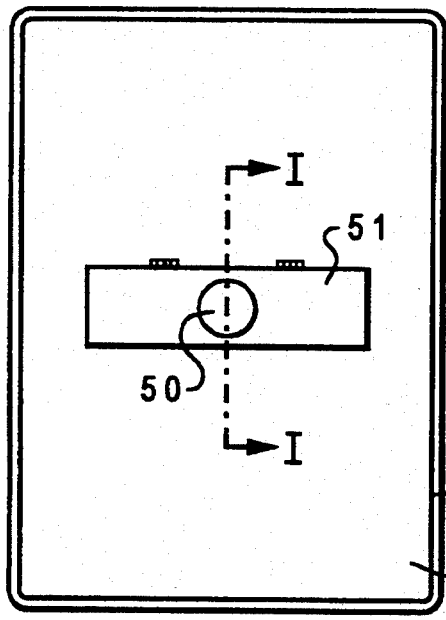
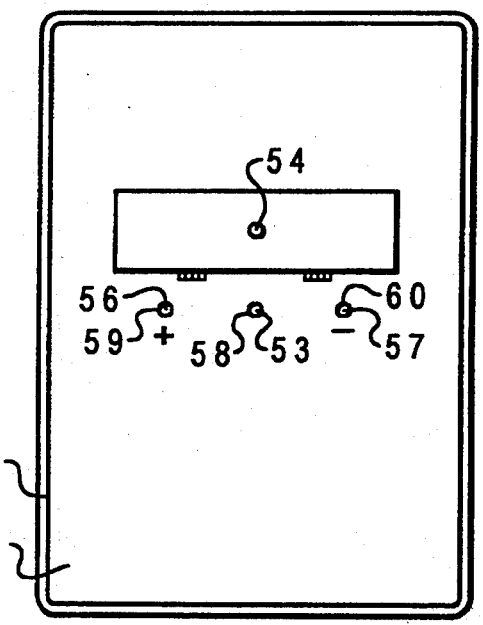
Fig. 5a         Fig. 5b
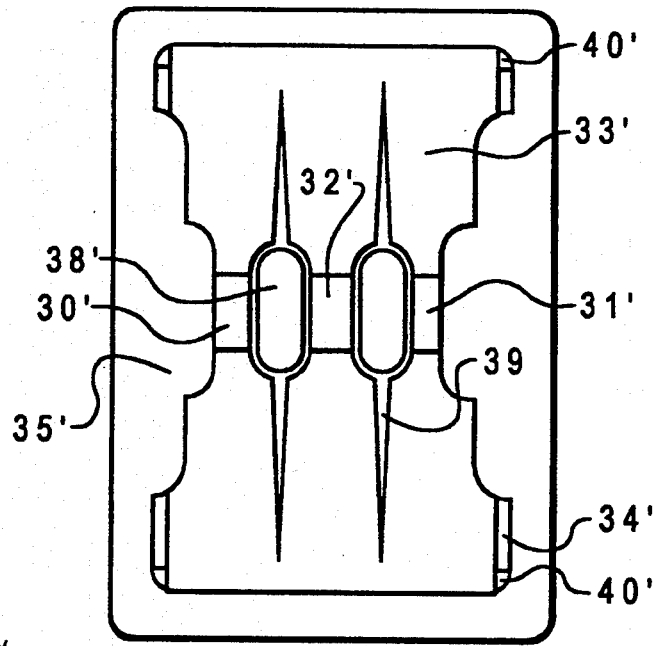
Fig. 7

DEVICE FOR ANALYSIS FOR CONSTITUENTS IN BIOLOGICAL FLUIDS

This application is a continuation of application Ser. No. 07/451,768 filed Dec. 18, 1989 now abandoned.

BACKGROUND OF THE INVENTION

1. Field of the Invention

This invention relates to a device and method for separating blood cells from biological fluids and, subsequently, assaying for a constituent in the remaining fluid, and particularly separating blood cells from whole blood and assaying for a constitutent that may be present in the plasma. Specifically, this invention relates to a self-contained device and method for analyzing very small samples of whole blood either semi-quantitatively or qualitatively.

2. Description of Related Art Including Information Disclosure Statement

Medicine has growing demands for quick, accurate determination of analytes in biological fluids and especially blood plasma. Traditionally, assays for analytes have been performed by laboratories and required skilled technicians, complex apparatuses, multi-step procedures requiring a plurality of reagents, and considerable time in order to determine results.

Numerous qualitative and some quantitative devices and methods have been developed which eliminate or decrease the need for skilled technicians in the analysis of analytes in blood plasma. Many of these devices and methods are test strips or dip sticks which, when exposed to blood, plasma, or other body fluids, measure an analyte in order to obtain a diagnostic result. A common example of this technology includes the various test products for determining the level of blood glucose in diabetics. These tests are conducted by comparing the amount of color formation of the dip stick or paper strip to a standard or color chart. The convenience of many of these tests does not always eliminate their complexity nor the requirement that the test be performed by skilled, medical personnel.

Analytes in whole blood are, ordinarily, measured after the red blood cells are separated from the plasma. This separation is particularly important with detection methods that depend on a color change. The presence of red blood cells in these tests interferes with the color determination. The red blood cells can also interfere with the measurement of an analyte by participating in a chemical reaction with the test reagents.

Accepted technologies for separating plasma from blood cells include centrifugation, agglutination, and filtration. These technologies, typically, require manual operations and, because they have several steps, can introduce health risks that are associated with the handling of blood and blood products. In the case of centrifugation, the equipment is expensive. Filtration is slow and wastes sample because cells tend to collect in the filter pores and impede the passage of plasma through the filter.

Methods that require a transfer of blood sample from one device to another can require relatively large sample volumes. These sample volumes can be on the order of milliliters and are required in part because of sample losses that occur during the transfer of blood. A sample of this volume requires collection by venipuncture rather than a skin prick. Venipuncture is undesirable because it is more invasive to the patient and requires skill in order to be safely performed.

A number of products have been developed that measure analytes in whole blood whereby plasma separation occurs within the device. Most of these products filter the red blood cells from plasma. Such products include the Syntex product sold under the trade name "Acculevel," the Chematic Inc. products sold under the trade name "Chemcard," the Ames Blood Glucose Sticks product, the Reflatron Cholesterol test product, the Hybritech product sold under the trade name "ICON/CITE," and the Abbott product sold under the trade name "TestPack." Commercial blood analyte test products have the undesirable characteristics of producing inconsistent results or requiring relatively large blood samples. Inconsistent results can be either variations between various test kits in actual readings of an analyte from a common blood sample or variations in the color development of a chromatic reaction within a single test kit.

Inconsistent test results are sometime caused by incomplete separation of blood cells and plasma. The presence of red blood cells in the reagents causes inaccurate measurement of the plasma sample and, in the case of glucose sticks, makes additional procedural manipulations necessary. Many products do not have efficient flow of plasma through the blood separation portion of the device. This results in slow test results and in uneven application or exposure of sample to the reagents and, therefore, uneven reaction color.

The requirement by certain commercial products for relatively large blood samples can be due to many factors. One such factor is that plasma is often retained in the blood cell and plasma separation element of a device. This requires a relatively large blood sample be drawn from the patient in order to provide sufficient plasma to the reagent zone of the device. For example, many of these commercial devices require "several drops" or from 200 to 300 $\mu$l of whole blood. A small skin prick by a needle, typically, is not satisfactory to obtain this volume of blood. In contrast, the product sold under the trade name "Acculevel" requires only a small sample of precisely 35 $\mu$l. Dispensing such a small sample requires manual dexterity and practice. Therefore, this test does not lend itself to use by lay persons.

U.S. Pat. No. 3,552,925 to Fetter discloses a method for separating whole blood into a substantially colorless fluid and the red cell components or residue. Whole blood is contacted with a matrix containing a water-soluble salt having an inorganic cation such as potassium citrate, ammonium sulfate, zinc sulfate, or the like. A preferred embodiment has a matrix containing one of these salts positioned adjacent to a reaction layer. The inventors do not disclose use of any substance other than inorganic salts to separate the red blood cells.

U.S. Pat. No. 4,594,327 to Zuk discloses an assay method for whole blood samples. This invention uses at least one specific binding pair which is substantially uniformly bound to a solid bibulous element. The method of using this invention requires that the blood sample be mixed with an agent that binds red blood cells, and possibly other ingredients, to form an assay medium. When the analyte is being drawn into the device, blood cells aggregate at an air-liquid interface. This invention also requires a signal producing system in order to evaluate the rest results and does not provide a self-contained unit that can semi-quantitatively determine concentration of an analyte in a single step.

U.S. Pat. No. 4,477,575 to Vogel et al. discloses a process and composition for separating plasma from whole blood. The composition includes glass fibers having an average diameter of from 0.2 to 5 microns and a density of 0.1 to 0.5 grams per cubic centimeter. The process includes the steps of slowly trickling whole blood onto one side of a layer composed of a composition of glass fibers whereby plasma separated from the blood becomes available at another side of the layer. The total volume of the plasma separated from the blood is limited to at most 50% of the void volume of the glass fiber layer. The glass fiber layer is removed after the plasma has had time to enter the reaction layer. Separation can be improved by adding an absorbent layer that wicks plasma to a reaction layer. However, this increases the sample volume and time required to perform a test. The glass fibers of this device rely on filtration. Therefore, serum is trapped in the device and separation efficiency is poor.

U.S. Pat. No. 4,678,757 to Rapkin et al. discloses a device and method for whole blood separation and analysis. The whole blood is introduced to a carrier containing a carbohydrate layer which rapidly separates fluid from cellular fractions. In a preferred embodiment, the device is fabricated in a sandwich design containing layers of carbohydrate and reagent material between two layers of plastic. Various configurations are described and several provide multiple analyses per device. Permeable or impermeable carriers can also be used. The preferred permeable carriers are "absorbent materials," such as filter paper, felts, and fleeces. Carbohydrate solutions are applied and permeable carrier dried. The carbohydrate with impermeable carriers is applied to the carrier as a suspended powder. The preferred embodiment of this invention uses absorbent materials that reduce the amount of plasma that is released for a given volume of a whole blood sample.

U.S. Pat. No. 4,696,797 to Kelton discloses a blood separating device wherein a filter body is used having a porosity small enough to physically trap blood particles on the filter.

U.S. Pat. No. 3,983,005 to Goodhue et al. discloses a device for the analysis of cholesterol. The device has at least two layers. One layer spreads the sample and the other layer contains reagents for the analysis. Cholesterol oxidase and cholesterol ester hydrolyzing components can be present in either of these two layers. The use of this device requires the prior separation of blood cells from a whole blood sample.

U.S. Pat. Nos. 3,964,871 and 4,042,329 to Hochstrasser disclose methods and devices for detecting glucose and cholesterol. The devices of these disclosures are dipped into a sample of essentially cell-free body fluid. The device has a built-in color intensity scale. The distance along the scale for which there is a color change is directly correlated to analyte concentration and allows a semi-quantitative determination of analyte. This device requires a separation of plasma from whole blood before use and requires a blood sample on the order of milliliters rather than microliters in order to perform the test.

U.S. Pat. No. 4,160,008 to Fenochetti describes a device that analyzes a sample for several analytes on a common support. Each test region is isolated above the common support. A blotter is provided on the support to insure against run-off and cross-contaimination of analytical reagents.

U.S. Pat. No. 4,435,504 to Zuk et al. discloses an immunochromatographic assay with a support having bound "MIP" or antibody and a second enzyme. This invention measures the amount of analyte in a sample solution of a body fluid. This measurement is conducted by combining a premeasured volume of sample with a premeasured volume of a solution of enzyme labelled analyte and immunochromatographing the solution or employing a combination of enzymes wherein one enzyme is label and the other enzyme is affixed to the chromatographic support. The assay of this invention is performed by contacting the immunochromatograph with the sample containing solution. The sample traverses a region of the immunochromatograph by elution or solvent transport. The device used in this assay has a region in which the antibody is non-diffusively bound to a bibulous support. The analyte from the same and its enzyme labelled conjugate traverses this zone along with the solvent. The analyte becomes bound to the support through the intermediacy of antibody complex formation. The signal producing system provides the area in this region with a color change which identifies the distance from a predetermined point over which the analyte and its enzyme labelled conjugate have traveled. In this manners a quantitative determination of the analyte can be made. This invention does not directly test whole blood and requires accurate volumetric measurement of the blood sample and the enzyme conjugate solution and dilution of the blood sample by a separately applied solvent. Furthermore, the determination of the analyte concentration with this invention requires a "signal producing system" involving the absorption or emission or electromagnetic radiation such as ultraviolet light. The invention of this disclosure does not provide an immediate determination of the concentration of an analyte.

An article by Sloan et al. discloses "The Quantab Strip in the Measurement of Urinary Chloride and Sodium Concentrations" *Clin. Chem.* 30 (10), 1705–1707 (1984). The test strip of this disclosure provides a quantitative measurement of chloride and sodium concentrations in urine. The test strips of this invention rely on wicking alone, and typically require 15 to 20 minutes to fill the measurement zone. This device does not provide a rapid test nor a means for separation of cells.

Another area of art related to this invention is the elimination of blotchiness in color development of analyte tests. Blotchiness is a common problem with many devices. A representative example of this problem is sometimes displayed by the product sold under the trade name "Chemicard" which is manufactured by Chematics in North Webster, Indiana. This test conveniently measures cholesterol in three minutes from a drop of whole blood. The developed color readings of this product are sometimes blotchy and, therefore, difficult to read.

The product sold under the trade name "Chemicard" uses a drop of blood in a test area. The test area is a small porous pad supported at its periphery by a card that covers most of the device. A membrane is attached beneath the test area to a small support. The small support is also attached to the top card. The membrane keeps most blood cells from reaching the reaction pad. The reaction pad is supported by a card and surrounded by a color wheel. After three minutes, the top card and membrane are removed and the reaction pad compared with the color wheel. Six color intensities for cholesterol levels ranging from 150 to 300 mg/dl are indicated by this test. A significant number of users of this product in an independent survey expressed dissatisfaction with readability of the results of the test because the developed color is so blotchy.

The industry lacks an accurate self-contained means for analyzing of plasma constitutents that uses a small quantity of whole blood and that is fast and accurate and can be used by the patient for self-testing.

SUMMARY OF THE INVENTION

The invention is a device for separating blood particulates from biological fluids and, particularly, plasma from whole blood. The invention includes nonabsorbent, porous unitary separator means, which is desirably made of glass fibers, containing a blood cell binding composition, such as a lectin, at a concentration or amount sufficient or effective to bind blood cells. The invention is also a device for measuring a plasma analyte in whole blood. This device has a base and at least one separator means thereon for separating plasma from whole blood. The separator means comprises (i) a nonabsorbent, porous unitary support and (ii) a blood cell binding composition in an amount sufficient to bind blood cells. The device further has at least one reaction pad on the base in fluid-flow communication with the separator means to receive the plasma therefrom. The reaction pad has a means for detecting the analyte, such as a chromatic chemical indicator. A desirable embodiment of the device has pressure-producing means over the reaction pad for applying uniaxial pressure to the reaction pad which is sufficient to control migration of the plasma through the reaction pad to produce a homogeneous result.

The invention further comprises a method for obtaining plasma from whole blood. The method involves separating the whole blood in a nonabsorbent, porous unitary separator means containing a blood cell binding composition. The method then includes collecting the separated plasma.

The invention is also a method for measuring an analyte in plasma. This method involves separating plasma from whole blood with a nonabsorbent, porous unitary separator means containing a blood cell binding composition. The method then includes absorbing the plasma in a reaction pad in fluid-flow communication with the separator means having means for detecting the analyte. The plasma is adsorbed in the reaction pad within 5 minutes. The method further includes calculating the concentration of the analyte in the reaction pad by comparison with a standard.

BRIEF DESCRIPTION OF THE DRAWINGS

FIGS. 5a and 5b are plan views of a device with a reaction site and two control sites to which reagent, wash, and indicator solutions are added, and for which the separator pad is contained in a detachable lid. FIG. 6 is a partial secitional view of the detachable lid of FIG. 5a containing a separator pad and transfer material taken along line I—I of FIG. 5a.

FIG. 7 is a cut-away view of a device for which the separator pad is contained in a detachable lid and which contains a reaction site and control sites to which reagent, wash, and indicator solutions are added.

DESCRIPTION OF THE PREFERRED EMBODIMENTS

Figure 1:
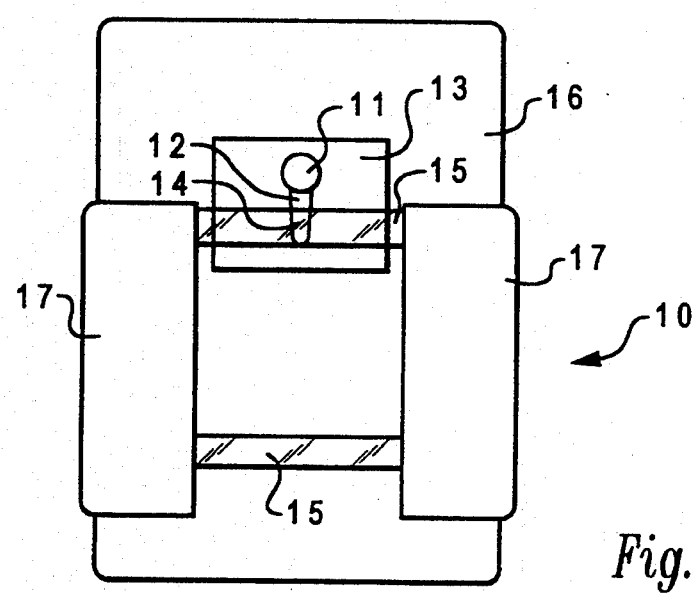
FIG. 1 is a top plan view of the preferred embodiment of a device of this invention.

While the invention is suitable for use with any blood-cell containing biological fluid, such as blood-containing spinal fluid and urine, it is particularly suitable for use with whole blood specimens and will be described in connection therewith.

The invention directed to device for separating plasma from whole blood comprises a nonabsorbent, porous unitary separator means, which is desirably made of glass fiber, containing a blood cell binding composition, such as a lectin. This device provides a test kit for measuring a plasma analyte in whole blood. This kit separates plasma from the whole blood, exposes the plasma to reactants that detect an analyte, and provides a chromatic or other indicator means in response to exposure to the analyte. A desirable embodiment of the device has a pressure-producing means over the reaction pad to apply uniaxial pressure to the reaction pad. The pressure enhances or controls migration of plasma to ensure substantially uniform spread thereof across the reaction zone on the reaction pad. The invention also includes a method for separating plasma from whole blood and a method for detecting an analyte. The device and method of this invention are suitable for assaying an analyte that is a member selected from the group consisting of cholesterol, a hormone, a pharmaceutical, an antibody, an antigen, a hapten, an infectious organism, and DNA hybridization particles.

While the nonabsorbent, porous support is desirably made of glass fiber, other materials, including fibrous and nonfibrous filters, can be used. The amount of absorbency and porosity of a particular support can vary according to the needs of a particular device. The selection of these characteristics for a particular support is, generally, within the skill of the art. These characteristics must be selected in order to enhance the function of the support with the blood cell binding composition to inhibit the passage of cellular material through the support.

Desirable nonabsorbent, porous supports that are suitable for use in this invention, are commercially available. Glass filters that are suitable for use with this invention include products sold under the trade names Whatman GF/D, Whatman BSB-45, and S&S No. 40. These glass filters have large pore sizes that permit red blood cells to pass through the filter. Glass filters with smaller pore sizes, such as those sold under the trade names S&S No. 30, Millipore AP20, and Millipore AP40, release plasma considerably slower and can adversely effect test results. The porosity of the support must be of a size to permit efficient transfer of plasma through the support.

The blood cell binding composition that is used with the device of this invention is a substance that can be encased, adsorbed, coated, or otherwise held by the nonabsorbent, porous support of this invention. The blood cell binding composition, in an amount sufficient to bind red blood cells, must combine with or adhere to blood cells or blood cell particles in order to inhibit the blood particles from passing through the support. The most desirable blood cell composition is provided by agglutinates and by antibodies to red blood cells. Agglutinates are desirably hemagglutinins. Hemagglutinins are "sugar-binding proteins" or "glycoproteins" of nonimmune origin which agglutinate cells and/or precipitate glycoconjugates. The preferred embodiment of the invention uses a lectin that can bind all the blood cells of the animal species being tested. Such lectins are well known. For use with human blood specimens it is preferred to use the lectin isolated from *Triticum vulgaris* (wheat germ) as the blood cell agglutinator. Antibodies to red blood cells can be derived according to the art and are desirably monoclonal antibodies.

The device for separating plasma from whole blood of this invention is suitable for use in a self-contained, chromatic semi-quantitative analyzer. The device for separating plasma can also be used to separate plasma from whole blood for other purposes. The plasma can then be used with a separate chromatic chemical indicator or enzyme linked immunoassay (EIA) to detect an analyte.

The invention includes a device for analyzing a plasma analyte or measuring a plasma analyte for subsequent analyzing from small quantities of whole blood. This device has a means for separating plasma from whole blood. The means for separating has a nonabsorbent, porous support in which is contained a substance that binds blood cells. This support is mounted on a base and is positioned such that filtered fluid from the support flows into contact with a reaction pad. Blood cells are trapped by the support and plasma flows freely through the support to the reaction pad. The pore size of the support is so large that, without the blood cell binding substance, the blood cells pass through the support. A sufficiently large enough pore size is required in order to permit rapid flow of plasma or other body fluid through the support. The support or separator pad can be removed after transfer has occurred.

The device for measuring or analyzing a plasma analyte according to this invention has a reaction pad with a reaction zone. The reaction zone can encompass the entire viewable area of the pad or only a portion thereof. The reaction pad contains at least one reactive substance. The reactive substance(s) can be a reagent and/or an indicator that reacts with a desired analyte. The reactive substance(s) can be in zones on the reaction pad and applied by a fluid sprayer, dipping, or other suitable means. The application of the reaction substance(s) is at a concentration that produces a chromatic or other qualitative or quantitative reaction within the range of expected plasma concentration or the desired analyte. When more than one reactive substance is applied to a reaction pad, the different reactive substances are applied to the reaction pad that mixes one reaction substance before the next reaction substance in a reaction sequence.

Certain embodiments of the device do not incorporate any or all reaction substances into the reaction pad. These embodiments, typically, are accompanied by separately packaged vials of reaction substances that are sequentially added to the reaction pad either before or after depositing the whole blood sample. The reaction pad in these embodiments is a "reaction site".

The reaction pad of the device for measuring or analyzing a plasma analyte of this invention desirably produces a chromatic reaction with the analyte. The hue and/or intensity of the chromatic reaction can be correlated to the concentration of the analyte. This embodiment of the invention produces a semi-quantitative analysis or end point for the analyte. The most desirable embodiments of this invention have at least two reaction pads. One of these two reaction pads provides a standard or calibration standard for the test solution reaction pad.

The desirable embodiment of the invention uses wicking means. The wicking means is desirably a strip of material and has a first end and a second end. The means for separating plasma from blood cells is in fluid-flow communication, as by being in contact with or juxtaposed to, a first end of the wicking means. The other end of the wicking means is in fluid-flow communication; i.e., contact with or juxtaposed to, the reaction pad of the device. The wicking means is desirably a wettable, nonabsorbent membrane. A commercially available product that is suitable for the wicking of this invention is sold by Millipore under the trade name Durapore. This product is hydrophilic and is available in numerous pore sizes. Desirable pore sizes that are suitable for use in this invention are 0.5 microns and 0.65 microns.

This invention includes a means for applying uniaxial pressure to the reaction pad and/or wicking means. The pressure applied by the means must be sufficient to control migration or flow of the plasma or body fluid through the reaction pad in order to produce a uniform distribution and hence a homogenous reaction across the entire reaction zone. Such pressure-producing means are particularly suitable in chromatic tests for cholesterol levels in blood specimens where uniformity of color in the reaction zone is important. The pressure applied can vary widely dependent upon the size of the blood specimen, the thickness of the pad and the like. However, a suitable pressure is between about 0.3 $Kg/cm^2$ and 0.7 $Kg/cm^2$ and preferably about 0.5 $Kg/cm^2$. The means for applying pressure is desirably a mechanical clasp means, but can be provided by screws or other usual means for applying comparable pressure.

A desirable embodiment of the invention uses the application of whole blood to the separator pad to provide plasma to a reaction site to which one or more reagents and/or indicators are then added. Desirably, blotting materials are connected to the reaction site and can also be brought into contact with the separation pad or reaction site to absorb excess reagent. The separator pad and the transfer material can be removed after transfer has occurred. For example, a test for feline leukemia virus transfers plasma to a reaction site. If the reaction site is recessed, a connection piece can be used to transfer plasma to the reaction site.

The reagents and indicators necessary for conducting a measurement or assay of this invention to an observable end point are those well-known in the immunoassay art and are commercially available. It is desirable that the reaction end point be observable without expensive equipment and that the reaction providing the reaction end point be completed within a short period of time, about thirty minutes or less. A preferred reaction end point is a color change that can be interpreted by a lay person and is observable within three minutes of introducing a blood sample to the device.

Reagents can be used in a reaction pad to analyze for one! of a variety of analytes, including haptens, sugars, cholesterol, antibodies, antigens, and viruses. Reagents for such assays, that rely on color indicators, usually require the user to distinguish shades, hues, or intensities of colors. These reaction colors are usually blue-green. Reagents for cholesterol assays, for example, produce a color variation from light blue to brown which, respectively, represent low cholesterol concentration to a high cholesterol concentration. This color range is especially useful for tests in which the concentration range between a low and a high concentration of an analyte is small and accuracy is important. An example of such an assay is an assay for cholesterol. An acceptable concentration of cholesterol is below 200 milligrams per deciliter and a dangerously high level is about 240 milligrams per deciliter. A change in colors at a critical boundary reduces the likelihood of misreading test results.

FIG. 1 depicts an embodiment of the invention that is a self-contained device 10 which semi-quantitatively detects an analyte in whole blood. The invention comprises blood-plasma separator means 11, preferably a pad made of glass fibers coated with a blood cell binding composition. Plasma separator pad 11 is atop transfer means 12, said means capable of wicking plasma from pad 11. Both of these are atop affixing means 13, such as an adhesive or a piece of double-sided tape. Transfer means 12 is in contact with a reagent and indicator-containing reaction pad 14. Transparent cover 15 is placed over reaction pad 14, and a portion of transfer means 12. A "squeezing" force is applied to the transparent cover 15 and, thereby, applies pressure to the reaction pad 14 and transfer material 12. Uniform pressurization can be achieved by clipping transparent cover 15 to rigid base 16 with a mechanical clasp means 17.

Separator pad 11 sits atop transfer means 12 which wicks plasma to reaction pad 14. Transfer means 12 in this embodiment is a strip with separator pad 11 atop one end and reaction pad 14 atop the other end. Desirably, transfer means 12 is a wettable, hydrophilic membrane such as the volume of sample retained by transfer means 12 is very small. Preferably, transfer means 12 is prepared from the commercial product sold under the trade name Durapore by Millipore.

Figure 2:
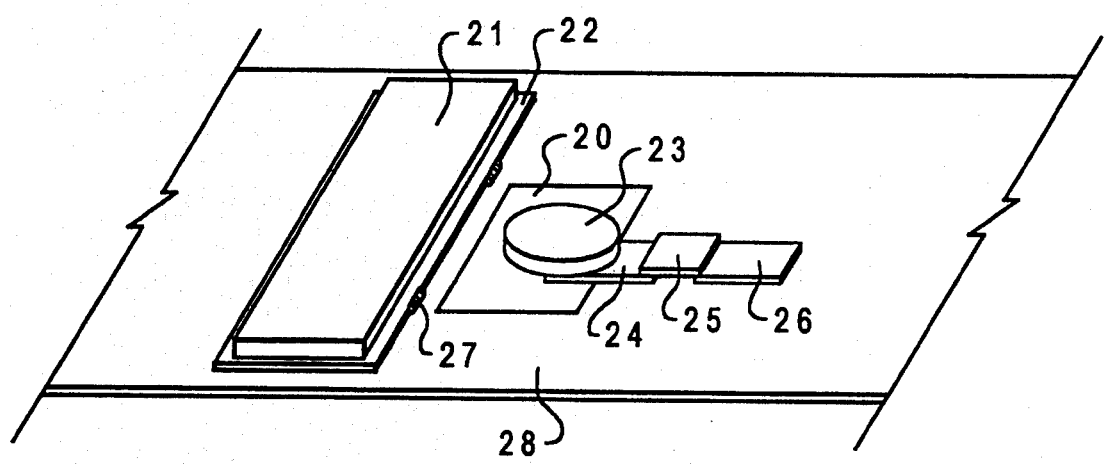
FIG. 2 is a perspective view of an alternate embodiment of the invention.

FIG. 2 illustrates a desirable embodiment of the invention in which plasma is transferred to a reaction site to which reagents must be added. Some reagents can be contained in the reaction site before the plasma is introduced. This device is particularly useful when immobilized reagents cannot be stored under conditions that expose them to air or when the reagents must be added stepwise in order for the assay to be conducted.

Separator pad 23 contains a support and blood cell binding composition is positioned atop an end of transfer material 24. Both of these elements are affixed to rigid base 28 with a piece of double-sided tape 20. Reaction site 25 is at the other end of transfer material 24, part of which sits atop transfer material 24 and part of which sits atop reservoir material 26. After whole blood is placed on separator pad 23, plasma migrates to reaction sites 25. Lid 22, to which is affixed a blotting material 21, is rotatable about a hinge 27 so that the blotting material 21 selectively contacts separator pad 23.

Reservoir material 26, preferably a porous, fluid absorbing fibrous pad of the type used as adsorbent pads in assay devices, serves the function of absorbing waste solutions, thereby permitting the absorbing of a sequence of solutions applied to the reaction site 25. Blotting material 21 absorbs any colored components that are released if blood cells lyse. Reservoir material 21 and reservoir material 26 can be any wettable material that has sufficient capacity for the solutions to be dispensed. Reservoir material 26 is also fixed to rigid base 28 and in fluid-flow contact with reaction site 25.

Figure 3:
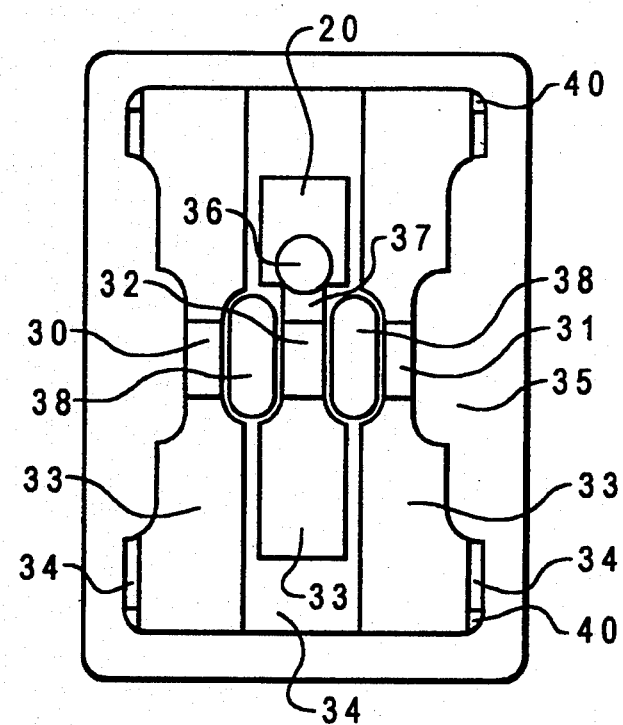
FIG. 3 is a cut-away view of an alternate device of the instant invention.

FIG. 3 illustrates an embodiment of the invention that is similar to the embodiment of FIG. 2. The embodiment of FIG. 3 has additional sites for positive control site 30 and negative control site 31. Such additional control sites can also be used for calibration of a semi-quantitative assay. The control sites require the same additional reagents and indicators as does reaction site 32 and, therefore, each is in contact with reservoir material 33 that lies within recessed portion 34 of rigid base 35. The dimensions of blotting material 33 can vary according to the assay to be performed. The dimensions depend on the quantity of fluid that must be absorbed. Portions of separator pad 36, reaction site 32, and control sites 30 and 31 are exposed for illustration purposes. Isolation means 38 which can integral with rigid base 35, act to prevent fluid flow between control site 30, control site 31 and reaction site 32. Means 38 can be upraised islands which isolate sites, 30, 31, and 32 from each other and made of any liquid impervious material, preferably plastic.

Figures 4A, 4B:
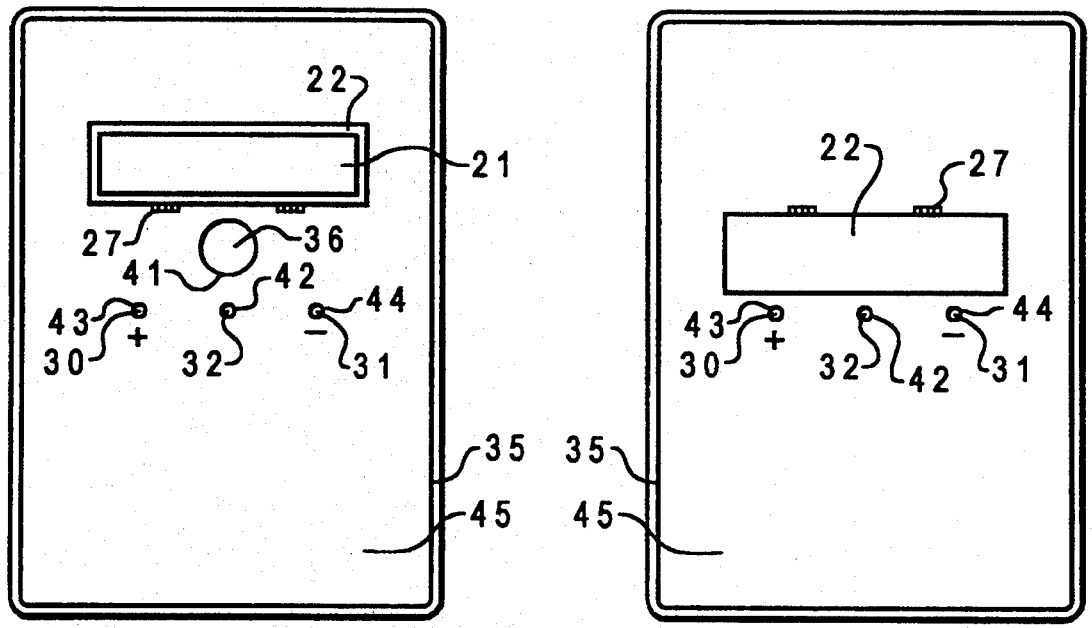
FIGS. 4a and 4b are top plan views of the device of FIG. 3 with a top cover and blotting means shown.

FIGS. 4a and 4b illustrate the embodiment of the invention of FIG. 3, but blotting material 33, transfer material 37, and portions of separator pad 36, reaction site 32, and control sites are protected and secured by cover 45. Reagents are introduced to the reaction sites and control sites and migrate into reservoir materials 33. Rigid base 35 has small vents 40 that lie within recessed portion 34 and are at the periphery or corners of the device. Vents 40 are provided to allow air to escape as fluid passes through the various membranes. Vents 40 are sealed to rigid base 35 by cover 45. A desirable rigid base 35 is commercially available under the trade name EZ-Screen Quik-Card Test and manufactured by Environmental Diagnostics, Inc. of Burlington, N.C.

FIGS. 4a and 4b illustrate the fully assembled device of FIG. 3. FIG. 4a depicts the open position of lid 22 and FIG. 4b depicts the closed position of the lid 22. FIGS. 4a and 4b also illustrate the openings 41, 42, 43, and 44 in cover 45 that lead to separator pad 36, reaction site 32, positive control site 30, and negative control site 31, respectively.

Cover 45 is desirably an adhesive label with openings over separation pad 36, reaction site 32, and the control sites. Desirable printed matter on the label includes the name of the device with appropriate trademarks, the address of the manufacturer, the lot numbers expiration date, and an indication as to which opening is for sample, which is for the positive control, and which is for the negative control. It is also desirable that the cover be made of a material that will accept pen, pencil, or marker notations.

Figure 6:
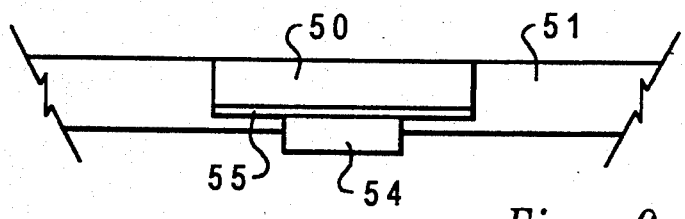

FIGS. 5a, 5b, 6, and 7 illustrate another embodiment of the invention. This embodiment of this device of the invention is similar to the device of FIGS. 4a and 4b except that separator pad 50 is contained in lid 51 rather than being attached to rigid base 52. This eliminates the need for blotting material in lid 51. After the plasma is released from separator pad 50, separator pad 50 and the lid 51 are disconnected from the reaction site 53. Transfer material 54 is used to connect separator pad 50 to the reaction site 53. Transfer material 54 is needed to ensure contact because the reaction pad (not shown) of this embodiment is slightly recessed as shown in FIG. 6. An optional transfer membrane 55 further improves transfer of the plasma from the separator pad 50 to transfer material 54. Positive and negative control sites, 56 and 57, respectively, and three openings 58, 59, and 60 in the cover 61 of this embodiment allow reagents and indicators to be added to reaction site 53 and the control sites.

FIG. 7 illustrates the embodiment wherein a single reservoir material 33' is used. In consequence of this, parts in FIG. 7 which are similar to those of FIG. 3 are identified with the same numerals, but with the inclusion of the prime symbol Rigid base 35', recessed area 34', reservoir material 33', and vents 40', depicted in FIG. 7 serve the same functions and have similar characteristics as the corresponding parts depicted in FIG. 3. The use of a single reservoir material 33' in which sites 30', 31' and 32' are separated by islands 38' and openings 39 in reservoir material 33' so there is no fluid-flow communication therebetween, makes for easier assembly of the device by lowering the number of parts that must be placed in proper relation to each other.

Figure 8:
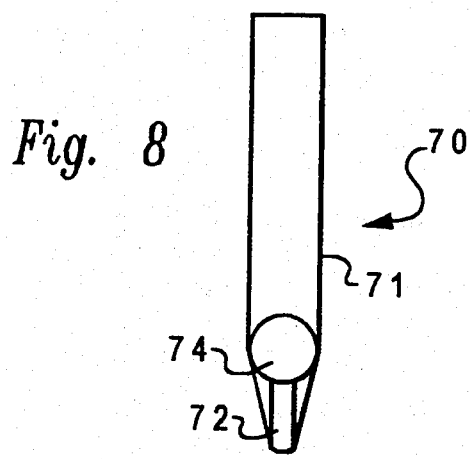
FIG. 8 is a top plan view of an alternate embodiment of a device of this invention.
Figure 9:
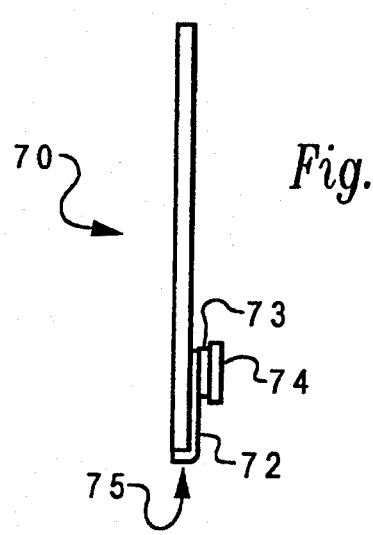
FIG. 9 is a side elevational view of the device of FIG. 8.

FIGS. 8 and 9 show in detail a blood separation device 70 comprising support 71, suitably made of wood, plastic, or metal, to which is attached, as by means of any fastening means, such as an adhesive or double-sided tape, transfer wicking means 72. Attached to an end of wicking means 72 is blood cell separator pad 73, preferably made of the same glass fibers as separator means 11 of FIG. 1 and also containing an agglutinator, preferably a lectin. Most suitably loading pad 74 is affixed, as by gluing at the edges, to pad 73 and acts to help distribute the blood specimen uniformly over the underlying surface of separator pad 73.

In use, the blood, most commonly 3 drops ($\sim 120$ $\mu l$) is placed on loading pad 74 and when it is noted that transfer wick 72 is saturated with plasma, the bottom 75 of wick 72 is placed in contact with the reaction zone of any conventional test device containing the reagents necessary to complete the assay. In this manner, the plasma is transferred to the reaction zone for completion of the assay. One suitable device is the EZ-Screen card discussed above. When the blood front reaches the bottom 75 of wick 72, device 70 is removed from the reaction zone and the assay completed on the reaction zone.

Figure 10:
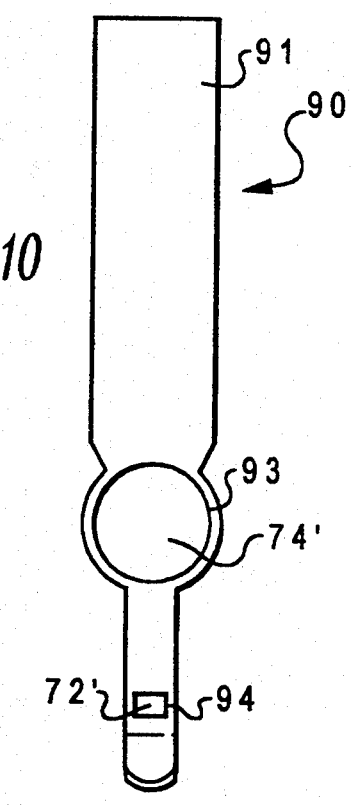
FIG. 10 is a top plan view of a modification of the device of FIG. 8.
Figure 11:
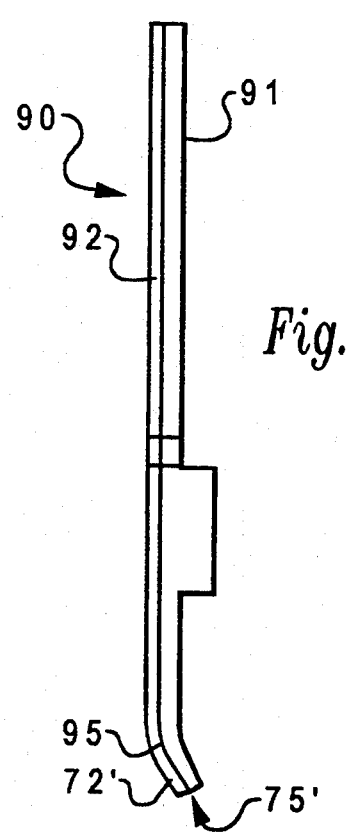
FIG. 11 is a side elevational view of the device of FIG. 10.

FIGS. 10 and 11 illustrate an alternate embodiment of the separator device of FIGS. 8 and 9 wherein the pads and wick are encased in a housing with only portions of the loading pad and wicking means visible. The housing can be made of metal, wood, or plastic, but is preferably made of plastic. As a consequence, parts in FIGS. 10 and 11 which are similar to those of FIGS. 8 and 9 are identified with the same numerals, but with the inclusion of the prime symbol. In this embodiment, in place of support 71 there is used housing 90 comprised of an upper half 91 and lower half 92. Upper half 91 has an opening 93 permitting the blood specimen to be placed on loading pad 74' and opening 94 permitting viewing of wick means 72'. Lower half 92 has an opening 95 which acts to expose the end 75' of wick means 72' thereby permitting the wick to be brought into contact with a reaction site in the same manner as the device of FIGS. 8 and 9. Opening 94 permits the user to monitor the flow of plasma along the wick and also to note when any blood (red) reaches that point so the device 90 can be removed from the reaction site.

As is depicted, the lower portion of housing 90 is bent, preferably at an angle of about 30° to 45°, in order to permit the user to more easily view wick means 72' through opening 94 when the device is applied to the reaction zone of any test device for completion of the assay.

Figure 12:
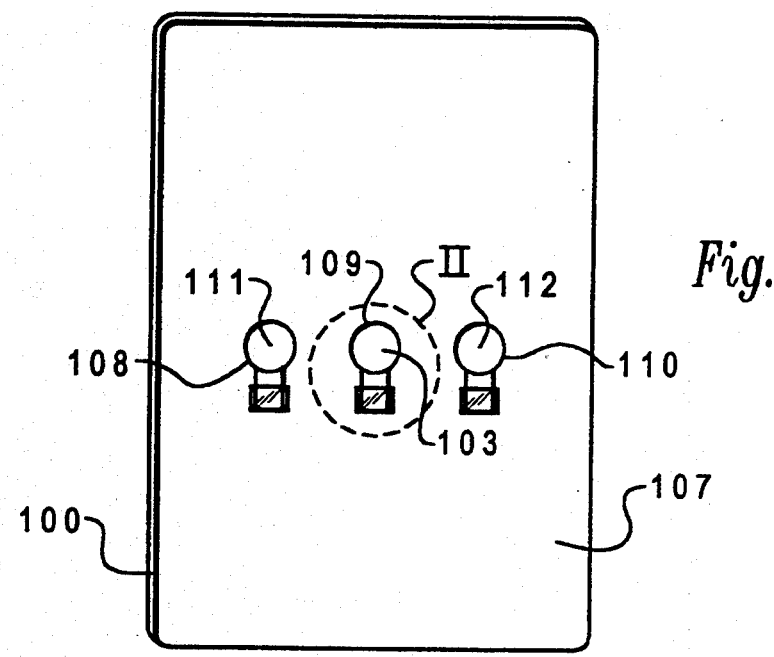
FIG. 12 is a top plan view of a device of this invention for testing for cholesterol.
Figure 13:
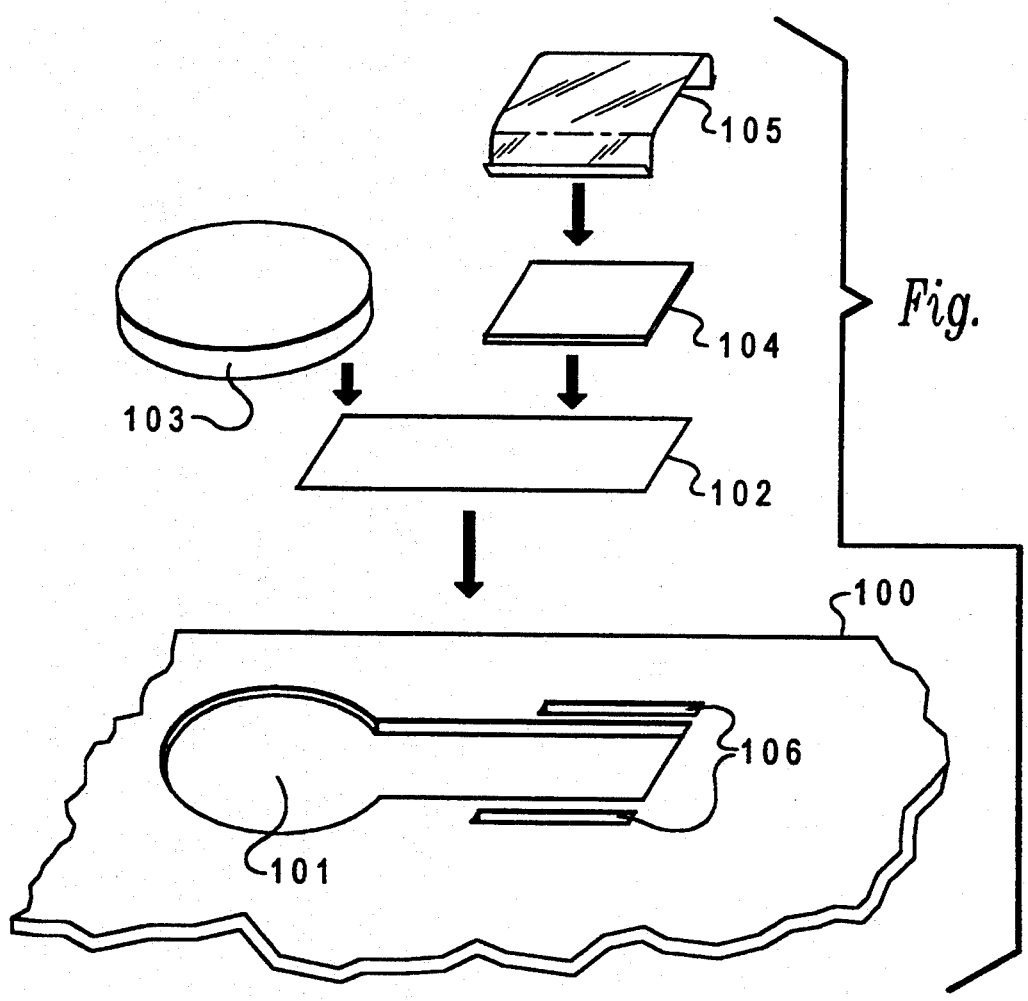
FIG. 13 is a partial exploded view of the device of FIG. 12 taken along dotted line II of FIG. 12.

FIGS. 12 and 13 illustrate a device in accordance with the present invention suitable for a cholesterol test. There is shown a base 100, preferably made of plastic, having depression 101 into which a seated transfer membrane 102 which is in fluid-flow communication therewith at one end with lectin-coated blood separator 103. Reagent pad 104 is atop the other end of transfer membrane 102 and over membrane 104 is a transparent cover means (preferably made of plastic) 105 having sides which snap-fit into grooves 106 in base 100 to maintain cover means 105 in place over reagent pad 103. FIG. 12 shows cover 107 over the components of the device having openings 108, 109, and 110 for access, respectively, to positive control separator 111, blood separator 103, and negative control separator 112 and the accompanying transfer membranes and reagent pads. It will be understood and is obvious that for the positive and negative control portions have transfer membranes, reagent pads, and transparent covers corresponding to 102, 104, and 105 and for the same purposes. Grooves 106 are deeper than the sides of cover means 105 enabling the upper surface of cover means 105 to be depressed thereby applying the necessary pressure to the reaction pad.

The invention will be further described in connection with the following examples which are set forth for purposes of illustration only.

EXAMPLE 1

Example 1 demonstrates the extent of red blood cell retention on a blood separator pad that is made according to this invention. This example demonstrates the effect of concentration of lectin contained in the blood separator pad. The procedures and results of this example are as follows:

Thirty $\frac{1}{4}$ inch disks were cut from a commercially available glass filter sold under the trade name Whatman GF/D. A first set of ten of these disks were coated with 35 $\mu l$ of a 5 milligram per milliliter (mg/ml) lectin solution. A second set of ten of these disks were coated with 35 microliter ($\mu l$) of a 2.5 mg/ml lectin solution (*Triticum vulgaris*). A third set of ten of these disks were coated with 35 $\mu l$ of a 1.25 mg/ml lectin solution. All three sets of coated disks were allowed to dry overnight at room temperature in a dry room.

Each disk was placed atop a 5×30 millimeter (mm) strip of a commercially available hydrophilic membrane sold under the trade name Duropore. A sample of 40 $\mu l$ of whole sheep blood (Alsevers treated) was spotted on each disk. Each disk was removed after 1 minute and the strips were examined for the presence of red blood cells and separated plasma. All thirty strips were saturated from end to end with plasma. Red blood cells appeared on certain strips as shown in Table I.

TABLE I

This table presents the effects of the concentration of lectin that is isolated from *Triticum vulgaris* on the retention of blood by separator pads made from Whatman GF/D glass filters. The results described in terms of visual red blood cell leakage.

| Set | Lectin Concentration/35 l | Results |
|---|---|---|
| 1 | 5 mg/ml | no leakage in 10 disks |
| 2 | 2.5 mg/ml | minor leakage in 3 disks |
| 3 | 1.25 mg/ml | leakage in 10 disks |

This example demonstrates that a coating of lectin in a concentration of at least about 2.5 mg/ml provides effective blood cell binding for the blood separator pad of this invention. A coating of lectin in a concentration of about 5 mg/ml is very desirable for the blood separator pad of this invention.

EXAMPLE 2

Example 2 provides a semi-quantitative test kit for a cholesterol assay. This example represents the preferred embodiment of the invention for the test kit for measuring an analyte. The procedures and results of this example are as follows.

Blood separation pads were prepared in 5/16 inch diameter circles. These blood separation pads were cut from a glass fiber filter sold under the trade name Whatman BSB-45. The circles were spotted with 15 $\mu$l of lectin solution in a concentration of 2 mg/ml. This lectin was isolated from wheat germ lectin (*Triticum vulgaris*) in phosphate buffer. The coated blood separation pads were dried overnight in a room with a relative humidity no higher than 15 percent.

Reaction pads were prepared in 3/16 inch wide strips from filter paper sold under the trade name Whatman No. 42. These reaction pads were dipped in an equivolume mixture of 3,3',5,5' tetramethylbenzidine free base in methanol, 0.6 mg/ml, and tetremethylbenzidine hydrocholoride in deionized water, and dried in an oven at 55 degrees Celsius (°C.) for 3 minutes. Strips of treated paper were then cut into ⅜ inch lengths and each piece spotted with 0.0045 ml of a solution containing 0.2 molar PIPES, which is a standard buffer with a pH of 6.8, 100 millimoles (mM) of magnesium aspartate, 20 mM of sodium cholate, 100 units per milliliter (U/ml) of cholesterol esterase, and 125 U/ml horseradish peroxidase. The pieces were then dried for 3 minutes at 55° C. Dried reaction pads were stored in the dark with a desiccant.

The rigid base of the device of the invention was fabricated from plastic sold under the trade name Plexiglass. The rigid base was fabricated with the dimensions of 3/16 inch deep by 1⅜ inches wide by 2½ inches long. The rigid base w side with a blank white label of the type used in the product sold under the trade name EZ-Screen test. A ⅛ inch by ⅜ inch piece of double-sided tape was placed about a third of the way from the top of the plexiglass as depicted in FIG. 1.

The transfer material is a membrane sold under the trade mark Duropore and is 3/16 inch wide by ½ inch long by 2.0 microns. The membrane was placed half way up in the center of the double-sided tape. The separation pad was then placed over the portion of transfer material that was on the double-sided tape. A reaction pad was then cut into two 3/16 inch squares. One square was placed over the free end of the transfer material. A ⅛ inch wide by 1⅜ inches long by 3/16 deep piece of plastic was placed over the reaction pad with a long side of the plastic being parallel to the bottom of the rigid base. A second piece of plastic having the same dimensions was placed about ¾ inch below the first piece of plastic. Two clamps, Boston No. 1, 1¼ inch, were placed on the long sides of the rigid base so as the two pieces of plastic were held on both sides.

The resulting device of this example is suitable for use as a self-contained test kit for a cholesterol assay.

EXAMPLE 3

Example 3 provides a method for a cholesterol assay. This example represents the preferred embodiment of the invention for measuring an analyte. The procedures and results of this example are as follows.

The kit of Example 2 was used by lay subjects. The subjects placed a drop of whole blood obtained by a finger-prick on a separation pad of the cholesterol test device. It is also possible to use about 3 $\mu$l of EDTA mixed with whole blood. The sample transfer typically took 50 to 80 seconds. A test result obtained for this example of more than 120 seconds indicated that the drop of blood sample was too small and the test was considered invalid.

Subjects were told that low plasma cholesterol levels produce a green-blue or green color that corresponds with levels up to approximately 200 milligrams per deciliter (mg/dl). High plasma cholesterol levels produce a brown color that corresponds with cholesterol levels above approximately 220 mg/dl. Moderate plasma cholesterol levels produce a green-brown color that corresponds to levels between 170 and 250 mg/dL.

The method of the test of this example separated the red blood cells from the whole blood sample that was deposited on the nonabsorbent, porous support having wheat germ lectin. The separated plasma was absorbed onto the reaction pad of the respective devices. The reaction pads produced the chromatic reactions described above. The average time of reaction was 5 minutes or less. The chromatic chemical reactions were then compared to a color chart to provide the respective blood cholesterol concentrations. Self-evaluations by 8 individuals produced the results shown in Table 2.

TABLE 2

Table 2 provides results from self-evaluations by eight individuals using an enzymatic assay.

| Color | Cholesterol Level (mg/dL) Enzymatic Assay |
|---|---|
| green | 137 |
| green | 172 |
| green-brown | 178 |
| green | 181 |
| green-brown | 201 |
| green-brown | 222 |
| brown | 254 |
| brown | 271 |

The subjects of this example were able to evaluate their cholesterol levels by using the semi-quantitative test kit to perform the method of this invention.

EXAMPLE 4

Example 5 provides a device for detecting antibodies to bovine serum albumin in whole blood. The device of this example has a reaction site wherein the reaction pad does not contain all the necessary reagents to conduct the assay and reagents must be added to the kit. The procedures and results of this example are as follows.

The device of this example was assembled so that the separator pad provides a means for supplying plasma to a reaction site. The device was assembled as depicted in FIGS. 2, 3, and 4. The assay used the following components from the commerically available EX-Screen aflotoxin test. The components were a substrate vial containing 4-chloro-1-naphthol, a wash vial containing phosphate buffered saline, and the rigid base.

Separation pads were made by cutting glass filters sold under the trade name Whatman GF/D into disks of ¼ inch diameter and laying them on a clean plastic surface. Four milligrams of wheat germ lectin were weighed and dissolved in 1 milliliter of phosphate buffered saline with sonication. Then, 35 microliters of this solution were placed on each disk and the disks were dried 12 to 18 hours in a room with a relative humidity of 6 to 12 percent.

Reaction sites were coated by cutting filter material sold under the trade name Whatman BSB-45 into 4 by 6 millimeter rectangles and placing them on a clean plastic surface. Five milligrams of commercially available bovine serum albumin was dissolved in 1 milliliter of phosphate buffered saline with sonication. Ten microliters of this solution was spotted onto each rectangle and allowed to dry for 12 to 18 hours in a room with a relative humidity of 6 to 12 percent.

The transfer material was prepared as a 4 by 7 millimeter rectangle of the Whatman BSB-45 filter material. The blotting material for the lid and reservoir material was the material sold under the trade name S&S 30 cut into 1 by 1.5 centimeter rectangles. The filter lid was also S&S 30 cut into a 1 by 3 centimeter rectangle and taped onto a cardboard lid.

The test was assembled as depicted in FIG. 3 and 4. The transfer material and reservoir material were first taped to the center of a plastic base about 4 millimeters apart using double-sided tape. The reaction site was placed on a bridge between these two pieces and the blood separator was placed atop the other end of the transfer material. The S&S 30 reservoir material was placed in the left and right portions of the recessed area as depicted in FIG. 3 and reaction sites were placed atop the blotting material. An adhesive label and openings as depicted in FIG. 4a was placed over the pieces, exposing only the blood separator pad and portions of the reaction and control sites. A lid with blotting material was taped to the cover in such a way that it opened and closed in a hinged manner.

The device was used with HRP-labeled goat anti-rabbit IgG diluted 1:100 in phosphate buffered saline. The positive control was made with purified anti-bovine serum albumin antibody diluted 1:5 in phosphate buffered saline. The negative control was phosphate buffered saline. The whole blood used for this example was human whole blood spiked at various concentrations with purified anti-bovine serum albumin antibody.

The test was begun with 50 microliters of blood sample being spotted on the separator pad and allowed to transfer to the reaction pad. Transfer took from 30 to 60 seconds. The lid and its attached blotting materials were then placed in contact with the separator pad. Then, 50 microliters of positive and negative controls were spotted at the appropriate, marked control sites (see, FIGS. 4a and 4b). Fifty microliters of goat anti-rabbit IgG HRP enzyme conjugate, commercially available from Sigma, was spotted on each of the three sites. One drop of wash solution from the EZ-Screen vial was spotted on each of the three test sites. Excess fluid was blotted from the edges of the test sites. One drop of substrate from the EZ-Screen vial was spotted on each of the three test sites. The results were read after 3 minutes.

A positive test result was indicated by the appearance of the blue-grey color on the test site. A negative result was indicated by the absence of color. Twelve tests were performed, three with anti-bovine serum albumin, three with anti-LKH, three with positive whole blood, and three with negative whole blood. Positive controls and negative controls always gave appropriate results.

TABLE 3

Table 3 provides results of twelve tests of the device for detecting antibodies to bovine serum albumin in whole blood.

| Sample | Replicate Test | | |
|---|---|---|---|
| | 1 | 2 | 3 |
| anti-BSA serum | + | + | + |
| anti-KLH serum | − | − | − |
| Positive whole blood | + | + | + |
| Negative whole blood | − | − | − |

Four additional tests were performed in which whole blood was spiked at various levels with purified anti-BSA antibody. Purified antibody was made by precipitation of anti-BSA rabbit serum with ammonium sulfate. This purified antibody is about three times more concentrated than it was in the serum.

A Minolta device sold under the trade name "Chroma meter" is a tristimulus color analyzer for measuring reflective colors of surfaces. This device was used to measure the "lightness factor" of the test site. The lightness factor is the percentage of light reflected based on a perfect reflectance of 100 percent. The smaller numbers equate to darker colors. In this test, a reading equal to or greater than 68 is considered negative. The results of these tests are summarized in Table 4.

TABLE 4

Tabale 4 provides results of four tests with the device for detecting antibodies to bovine serum albumin in whole blood. Color development serves as a function of dilution rate of purified antibody.

| | Test 1 | Test 2 | Test 3 | Test 4 |
|---|---|---|---|---|
| Dilution Factor | 1:5 | 1:10 | 1:20 | 1:100 |
| Percent Reflectance | 39 | 41 | 48 | 68 |

The device of this example detects antibodies from whole blood in small concentrations. This device is suitable for providing assays that can be read by detectors.

EXAMPLE 5

Example 6 provides a device for detecting feline leukemia virus in whole blood. The following device was assembled to incorporate the separator pad as a means of providing plasma to a reaction site. The device of this example is depicted in FIGS. 5a, 5b, 6, and 7. The procedures and results of this example are as follows.

The separator pads of this example were made by forming ¼ inch diameter circles cut from a sheet of filter material sold under the trade name Whatman GF/D using a hole punch. The pads were laid on a clean, plastic surface. Then, 5.0 milligrams of lectin from *Triticum vulgaris*, that is commercially available from Sigma, was dissolved with the aid of sonication in 1 ml of phosphate buffered saline solution. Each disk was spotted with 50 1 of lectin solution, the Disks were allowed to dry overnight in a dry room with a relative humidity of 6 to 12 percent.

A 10% Staph A solution of 100 microliters and a anti-feline leukemia virus antibody solution of 200 microliters, obtained from the company Synbiotics, were combined in a test tube, vortexed and allowed to incubate for 1 hour at 37° C. Separately, 40 microliters of a polysorbate and trehalose solution and 60 microliters of phosphate buffered saline were added and vortexed. A 10 microliter volume of the solution was then spotted onto the reaction site and the two control sites of approximately eleven EZ-Screen cards.

Purified feline leukemia virus antigen with an activity of 402 micrograms per milliliter was spiked into a bovine serum albumin solution and whole sheep blood (Alsevers treated) at varying concentrations Transfer material was placed atop the reaction site and a separator pad was placed atop the transfer material. The transfer material was used to ensure a good connection between the separator pad and the reaction site. A 40 microliter volume of whole blood spiked with feline leukemia virus antigen was placed on the separator pad. After 30 seconds, the separator pad and transfer material were removed. A 50 microliter volume of the control samples were added to the appropriate, marked site. This was followed by the sequence of a drop of conjugate on each of the three sites, one drop of wash solution per site, followed by wiping, followed by one drop of substrate per site. After 30 seconds, a reading was conducted with the Minolta chroma meter described above. Feline leukemia virus antigen was spiked into bovine serum albumin at concentrations from 400 to 40 nanograms per milliliter. The antigen was also spiked into whole blood samples at 200 and 0 nanograms per milliliter. Test results were as summarized in Table 5. In this test, a reading equal to or greater than 68 is considered negative.

What is claimed is:

1. A device for measuring a plasma analyte in whole blood comprising:
   (a) a base having horizontally disposed thereon,
   (b) at least one independent separating means on said base for separating plasma from whole blood, said separating means consisting essentially for (i) a porous unitary glass fiber support with a pore size large enough to permit blood cells to pass therethrough and (i) a blood cell binding composition in an amount sufficient to bind blood cells,
   (c) at least one independent reaction pad on said base in fluid-flow communication with a portion of and horizontally disposed from said separating means to receive said plasma from said separating means, said reaction pad having means for detecting said analyte, and
   (d) at least one independent reservoir material on said base in fluid-flow communication with a portion of each said reaction pad and extending horizontally therefrom, but not in fluid-flow communication with any said separating means.

2. The device of claim 1, wherein said porous support is composed of glass fibers.

3. The device of claim 1, wherein said blood cell binding composition is a lectin.

4. The device of claim 3, wherein said lectin is isolated from *Triticum vulgaris* and is adhered to said porous unitary support.

5. The device of claim 1, wherein said means for detecting said analyte is a chromatic chemical indicator capable of reacting with said analyte.

6. The device of claim 1, comprising at least two reaction pads, one of said two reaction pads providing a calibration standard for said analyte.

7. The device of claim 1, further comprising:
   (a) rigid means over said reaction pad but not in contact with said separating means for applying uniaxial pressure to said reaction pad, said pressure being sufficient to control migration of said plasma through said reaction pad to produce a substantially uniform reaction throughout said reaction pad.

8. A device for measuring a plasma analyte in whole blood consisting of:
   (a) a base having horizontally disposed thereon,
   (b) at least one independent separating means for separating plasma from whole blood, said separating means being on said base and comprising (i) a nonabsorbent, porous unitary glass fiber support with a pore size large enough to permit blood cells to pass therethrough and (ii) a lectin adhered to said porous support in an amount sufficient to bind blood cells,
   (c) at least one independent reaction pad on said base in communication with a portion of and horizontally disposed from said means for separating to receive plasma from said separating means, said reaction pad having a means for detecting said analyte,
   (d) at least one independent reservoir material on said base in fluid-flow communication with a portion of each said reaction pad and extending horizontally therefrom, but not in fluid-flow communication with any said separating means, and
   (e) a clear cover rigid plate over each said at least one reaction pad, said clear cover plate being a means for applying uniaxial pressure to each said reaction pad, said pressure being sufficient to control migration of said plasma through said reaction pad to produce substantially uniform reaction through each said reaction pad.

9. The device of claim 8, wherein said nonabsorbent porous support is composed of glass fibers.

10. The device of claim 8, wherein said lectin is isolated from *Tritricum vulgaris*.

11. A device for measuring an analyte in biological fluid containing blood cells comprising:
    (a) a base having horizontally disposed thereon,
    (b) an independent non-absorbent, porous unitary glass fiber support on said base having a pore size large enough to permit blood cells to pass therethrough and having a lectin adhered thereto,
    (c) at least one independent reaction pad on said base horizontally disposed from said support to receive said body fluid, said reaction pad having a means for detecting said analyte,
    (d) at least one independent reservoir material on said base in fluid-flow communication with a portion of each said reaction pad and extending horizontally therefrom, but not in fluid-flow communication with any said separating means, and
    (e) a rigid means for applying uniaxial pressure only to said reaction pad, said pressure being sufficient to control migration of said body fluid through said reaction pad to produce a substantially uniform reaction throughout said reaction pad.

12. The device of claim 11, wherein said means for applying pressure is a mechanical clamp means.

13. The device of claim 11, wherein said means for applying pressure is a cover plate adhered to said base.

* * * * *

UNITED STATES PATENT AND TRADEMARK OFFICE
CERTIFICATE OF CORRECTION

PATENT NO. : 5,435,970
DATED : July 25, 1995
INVENTOR(S) : Edward L. Mamenta; Michael F. Turnachik It is certified that error appears in the above-indentified patent and that said Letters Patent is hereby corrected as shown below:

Column 17, line 43, cancel "for" and substitute therefor --of--.

Signed and Sealed this

Twenty-sixth Day of September, 1995

Attest:

BRUCE LEHMAN

*Attesting Officer*  *Commissioner of Patents and Trademarks*